United States Patent [19]

Harper et al.

[11] Patent Number: 4,721,818

[45] Date of Patent: Jan. 26, 1988

[54] PURIFICATION OF POLYOLS PREPARED USING DOUBLE METAL CYANIDE COMPLEX CATALYSTS

[75] Inventors: Stephen D. Harper; Stephen H. Harris, both of West Chester, Pa.

[73] Assignee: Atlantic Richfield Company, Los Angeles, Calif.

[21] Appl. No.: 28,530

[22] Filed: Mar. 20, 1987

[51] Int. Cl.$^4$ .................. C07C 41/34; C07C 41/44; C07C 41/13
[52] U.S. Cl. ...................................... 568/120; 568/621
[58] Field of Search ................................ 568/620, 621

[56] References Cited

U.S. PATENT DOCUMENTS 4,355,188  10/1982  Herold ................................. 568/621

Primary Examiner—Howard T. Mars
Attorney, Agent, or Firm—Dennis M. Kozak

[57] ABSTRACT

A method for removing double metal cyanide complex catalyst residue from polyols using alkali metal hydrides is disclosed. In one embodiment, the catalyst residue is converted into an insoluble ionic metal species and separated by filtration using magnesium or aluminum silicate to facilitate separation.

12 Claims, No Drawings

PURIFICATION OF POLYOLS PREPARED USING DOUBLE METAL CYANIDE COMPLEX CATALYSTS

This invention relates to a process for the purification of polyols for use in the preparation of polyurethanes The preparation of polyols by the polymerization of alkylene oxides using catalysts of the double metal cyanide complex class is known. Also known is that the catalyst residues present in such polyols if not removed cause certain undesirable reactions forming volatile by-products which cause odor and other storage problems. U.S. Pat. No. 4,355,188 teaches that the removal of double metal cyanide catalyst residue can be accomplished by adding a strong base selected from potassium hydroxide, sodium hydroxide, potassium metal, and sodium metal.

The present invention provides another method for removing double metal cyanide complex catalyst residue from polyols involving the use of an alkali metal hydride.

According to this invention, there is provided a method for removing double metal cyanide complex catalyst residue from polyols which comprises after polyol formation the steps of: (a) incorporating into the catalyst residue-containing polyol an effective amount of an alkali metal hydride to convert the double metal cyanide complex catalyst into an insoluble ionic metal species separable from the polyol wherein the polyol hydroxyl groups are also converted to alkoxide groups; and (b) separating the insoluble ionic metal species from the polyol.

High molecular weight polyols suitable for use in the practice of this invention are typically prepared by polymerizing an alkylene oxide onto an initiator or telogen having at least one hydroxyl group using a double metal cyanide complex catalyst.

Any suitable telogen and alkylene oxide can be used. Suitable telogens for use to produce polyols usable in the invention include diols such as ethylene glycol, triols such as trimethylolpropane and glycerine, polyols such as pentaerythritol and various sugars. The preferred alkylene oxides are propylene oxide, 1,2-butylene oxide, and ethylene oxide.

The double metal cyanide complex class catalysts suitable for use and their preparation are described in U.S. Pat. Nos. 4,472,560 and 4,477,589 to Shell Chemical Company and U.S. Pat. Nos. 3,941,849 and 4,335,188 to General Tire & Rubber Company. The teachings of the foregoing patents are incorporated herein by reference.

One double metal cyanide complex catalyst found particularly suitable for use is a zinc hexacyanometallate of formula

$Zn_3[M(CN)_6]_2 \cdot xZnCl_2 \cdot yGLYME \cdot zH_2O$ wherein M may be Co(III), or Cr(III); x, y, and z may be fractional numbers, integers, or zero and vary depending on the exact method of preparation of the complex.

In one embodiment of the invention after the incorporation of the alkali metal hydride but before the insoluble ionic metal species is separated from the polyol, ethylene oxide is added to the mixture and the mixture is heated to convert the secondary hydroxyl groups of the polyol to primary hydroxyl groups.

Any suitable alkali metal hydride can be employed in the practice of the invention. Preferred alkali metal hydrides are sodium hydride, potassium hydride, and lithium hydride. The amount of hydride employed is that amount effective to convert the double metal cyanide complex catalyst residue into an insoluble ionic metal species. Broadly, molar ratios of hydroxyl groups on the polyol to alkali metal hydride of from 1:1 to 500:1 are contemplated. Although not required, in order to enhance the speed at which the insoluble ionic metal species forms it is desirable to heat the mixture. Heating at a temperature within the range of from about 40° C. to about 100° C. for up to five hours has been found advantageous.

Likewise, in the above-mentioned embodiment involving the additional step of end capping with ethylene oxide, heating the mixture serves to facilitate the reaction.

After the double metal cyanide complex catalyst residue has been converted to the insoluble ionic metal species, it can be separated from the polyol by conventional methods such as filtration using, for example, diatomaceous earth, or passing through an acidic ion exchange resin as taught in U.S. Pat. No. 4,355,188.

In yet another embodiment of this invention, it has been found that the insoluble ionic metal species can be easily separated from the polyol by filtration if a minor amount of magnesium silicate, aluminum silicate, or mixtures thereof, is incorporated into the mixture prior to separation. The silicate can be used alone or in combination with conventional filter aids such as diatomaceous earth. In addition to facilitating separation, it has been discovered that treatment with silicate also converts polyol alkoxide groups to hydroxyl groups and absorbs the resulting alkali metal hydroxide.

Typically, the amount of silicate added will be from about 1 to about 5 parts by weight per each 100 parts by weight of the polyol containing catalyst residue mixture and the mixture will be heated for 1 to 12 hours at a temperature of from about 80° C. to about 150° C. before filtration. It is preferred that the silicate be finely divided and have a high surface area. The addition of a small amount of water (0.1-3%) has been found to provide more reliable and quantitative catalyst removal.

The following examples further demonstrate the method of the invention.

EXAMPLE 1

A. Double Metal Cyanide Complex Catalyst Preparation

A solution of 4.15 g (12.5 mmole) potassium hexacyanocobaltate in 100 ml water was added slowly with good mixing to a mixture of 3.82 g (28.0 mmole) zinc chloride and 25.0 g 100-200 mesh alumina (United Catalysts SAHT-99) in 40 ml water. After addition was completed, 25 ml glyme was added and the mixture stirred for one hour. The catalyst was collected by filtration in a 6.5 cm diameter fritted filter funnel, washed 3 times with 70 ml 30% glyme and twice with 70 ml 90% glyme. Filtration required approximately 50 minutes and the filtrate was only slightly cloudy. The filter cake was air-dried, crushed, and dried 18 hours at 0.1 mm pressure at 25° C.

B. Polymerization

A one-liter stirred autoclave was charged with 2.23 g catalyst from A above, 21.5 g propoxylated trimethylolpropane (470 MW), 110 ml tetrahydrofuran (THF), and 32 g propylene oxide (PO). A pressure drop was observed shortly after heating the mixture to 90° C. Another 523 g of PO was added over 6 hours. Propylene oxide triols of approximately 10,000 molecular weight were prepared by this polymerization.

C. Catalyst Conversion

The reaction mixture obtained from B was cooled to 30°–40° C. and then treated with 0.62 g sodium hydride (NaH) for 3 hours at 75° C. to convert the catalyst to insoluble ionic species.

D. Ethoxylation

To the mixture from C was added 43 g ethylene oxide (EO) over a period of 5 hours at 75° C., and the mixture was allowed to react an additional 6 hours at 95° C. to ensure complete ethoxylation of the secondary hydroxyl groups to primary hydroxyl groups.

E. Purification of the Product Polyols

After removing the unreacted EO from the mixture from D, 50 ml THF and 17 g magnesium silicate were added to the reactor and the whole heated to 110° C. for 8 hours. The reaction products were then washed out of the reactor with THF and filtered. The small amounts of EO homopolymer formed were removed by stripping off the THF, diluting with hexane, and refiltering. The analysis of the final product is shown in Table I, Example 1.

EXAMPLE 2

The reaction mixture from Example 1B was cooled to 40° C. and then treated with 0.63 g potassium hydride (KH) for 1 hour at 75° C. Over the next 2.5 hours, 64 g EO was added at 75° C. and the mixture was allowed to react an additional 4 hours at 95° C. After removing the excess EO from the mixture, 50 ml THF and 17 g magnesium silicate were added to the reactor and heated to 110° C. for 8 hours. The product was worked up as in Example 1E, and the analysis of the final product is shown in Table I, Example 2.

EXAMPLE 3

To illustrate that the purification of the polyol by removal of the ionic species from the catalyst residues by treatment with magnesium silicate is equally applicable to the known reactions using alkali metal dispersions to reduce the catalyst, the following was done.

The reaction mixture from Example 1B was cooled to 40° C. and then treated with 0.61 g sodium dispersion (Na) for 3 hours at 75° C. Over the next 4.5 hours, 43 g EO was added at 75° C. and the mixture was allowed to react an additional 9 hours at 95° C. After removing the excess EO from the mixture, 50 ml THF and 17.5 g magnesium silicate were added to the reactor and heated to 110° C. for 8 hours. The product was worked up as in example 1E, and the analysis of the final product is shown in Table I, Example 3.

TABLE I

| Example No: | 1 | 2 | 3 |
|---|---|---|---|
| Metal used | NaH | KH | Na |
| $M_n$, Calc. | 12,400 | 12,100 | 11,700 |
| $M_n$, GPC | 8,200 | 8,870 | 9,620 |
| Hydroxyl No. | 16 | 17 | 17 |
| Unsat., meq/g | <0.01 | 0.004 | — |
| Wt. % EO | 5.6 | 5.5 | 3.6 |
| % Primary OH | 84 | 65 | 71 |
| Co, ppm | <1 | 6 | <1 |
| Zn, ppm | <0.5 | 5 | 0.5 |
| Na, ppm | 0.99 | — | 1.8 |
| K, ppm | — | 4.2 | — |

It will be evident from the foregoing that various modifications can be made to this invention. Such, however, are considered as being within the scope of the invention.

What is claimed is:

1. A method for removing double metal cyanide complex catalyst residue from polyols which comprises after polyol formation the steps of:
   (a) incorporating into the catalyst residue-containing polyol an effective amount of an alkali metal hydride to convert the double metal cyanide complex catalyst into an insoluble ionic metal species separable from the polyol wherein the polyol hydroxyl groups are also converted to alkoxide groups; and
   (b) separating the insoluble ionic metal species from the polyol.

2. The method of claim 1 in which said separating is accomplished by filtration.

3. The method of claim 1 in which said separating is accomplished by passing the mixture of catalyst residue-containing polyol and alkali metal hydride through an ion exchange resin.

4. The method of claim 1 in which said alkali metal hydride is sodium hydride.

5. The method of claim 1 in which said alkali metal hydride is potassium hydride.

6. The method of claim 1 in which said alkali metal hydride is a mixture of sodium and potassium hydride.

7. The method of claim 1 in which said alkali metal hydride is employed in a molar ratio of alkali metal hydride to hydroxyl groups on the polyol of from 1:1 to 1:500.

8. The method of claim 1 wherein the mixture of catalyst residue-containing polyol and alkali metal hydride prepared in step (a) is heated to enhance the speed at which the insoluble ionic metal species forms.

9. The method of claim 1 comprising after step (a) and before step (b) the step of incorporating an effective amount of ethylene oxide into the catalyst residue-containing polyol/alkali metal hydride mixture to convert the secondary hydroxyl groups of the polyol to primary hydroxyl groups.

10. The method of claim 1 wherein minor amount of aluminum silicate is introduced into the mixture and the insoluble ionic metal species is separated from the polyol in step (b) by filtration.

11. The method of claim 1 wherein a minor amount of magnesium silicate is introduced into the mixture and the insoluble ionic metal species is separated from the polyol by in step (b) filtration.

12. The method of claim 1 wherein a minor amount of a mixture of aluminum and magnesium silicate is introduced into the mixture and the insoluble ionic metal species is separated from the polyol in step (b) by filtration.

* * * * *